(12) United States Patent
Stoianovici et al.

(10) Patent No.: US 12,414,800 B2
(45) Date of Patent: Sep. 16, 2025

(54) NEEDLE-GUIDE ROBOT WITH PRESET DEPTH OF INSERTION

(71) Applicant: THE JOHNS HOPKINS UNIVERSITY, Baltimore, MD (US)

(72) Inventors: Dan Stoianovici, Reisterstown, MD (US); Doru Petrisor, Lutherville, MD (US)

(73) Assignee: The Johns Hopkins University, Baltimore, MD (US)

(*) Notice: Subject to any disclaimer, the term of this patent is extended or adjusted under 35 U.S.C. 154(b) by 310 days.

(21) Appl. No.: 17/855,428

(22) Filed: Jun. 30, 2022

(65) Prior Publication Data

US 2022/0330982 A1    Oct. 20, 2022

Related U.S. Application Data

(63) Continuation of application No. 16/303,673, filed as application No. PCT/US2017/033991 on May 23, 2017, now Pat. No. 11,439,434.

(60) Provisional application No. 62/340,006, filed on May 23, 2016.

(51) Int. Cl.
| | | |
|---|---|---|
| A61B 17/34 | (2006.01) | |
| A61B 10/02 | (2006.01) | |
| A61B 34/30 | (2016.01) | |
| A61B 50/30 | (2016.01) | |
| (Continued) | | |

(52) U.S. Cl.
CPC ...... *A61B 17/3494* (2013.01); *A61B 10/0233* (2013.01); *A61B 17/3403* (2013.01); *A61B 34/30* (2016.02); *A61B 50/30* (2016.02); *A61B 90/03* (2016.02); *A61B 90/08* (2016.02); *A61B 90/11* (2016.02); *A61B 90/37* (2016.02); *A61B 2017/3409* (2013.01); *A61B 2050/314* (2016.02); *A61B 2090/034* (2016.02); *A61B 2090/0813* (2016.02); *A61B 2090/374* (2016.02)

(58) Field of Classification Search
CPC ..... A61B 17/30; A61B 17/34; A61B 17/3494; A61B 17/3403; A61B 34/30; A61B 17/3417; A61B 17/3496; A61B 10/0233
See application file for complete search history.

(56) References Cited

U.S. PATENT DOCUMENTS

| | | | | |
|---|---|---|---|---|
| 5,916,175 A | * | 6/1999 | Bauer | A61B 10/0275 600/567 |
| 11,439,434 B2 | * | 9/2022 | Stoianovici | A61B 10/0233 |
| 2010/0049086 A1 | | 2/2010 | Johnson | |

(Continued)

OTHER PUBLICATIONS

Mozer, et al., Robotic Image-Guided Needle Interventions of the Prostate. Rev Urol. 2009 Winter, 11(1):7-15.

(Continued)

*Primary Examiner* — Vi X Nguyen

(57) ABSTRACT

An embodiment in accordance with the present invention provides a robot structure that includes an MM-Safe pneumatic stepper motor and optical encoding technologies. The present invention includes a needle guide and a needle depth limiter. The needle for biopsy is inserted through the needle guide and the depth of inserting is limited by the needle depth limiter. The robot is configured to control this procedure. The robot structure is adapted for biopsy, a novel way of setting the depth of needle insertion, image-to-robot registration. The system includes control for the robot.

6 Claims, 3 Drawing Sheets

(51) Int. Cl.
*A61B 90/00* (2016.01)
*A61B 90/11* (2016.01)

(56) References Cited

U.S. PATENT DOCUMENTS

2010/0160823 A1  6/2010 Parihar et al.
2015/0265354 A1* 9/2015 Stoianovici ........ A61B 10/0241
                                           600/417

OTHER PUBLICATIONS

Stoianovici, Technology Advances for Prostate Biopsy and Needle Therapies. J Urol. Oct. 2012;188(4):1074-5.
Taylor, et al., Medical robotics in computer-integrated surgery. IEEE Transactions on Robotics and Automation. Oct. 2003;19(5):765-781.
Blumberg, et al., The pullout strength of titanium alloy MRI-compatible and stainless steel MRI-incompatible Gardner-Wells tongs. Spine (Phila PA 1976). Oct. 1, 1993;18(13):1895-6.
Gassert, et al., MRI-Compatible Robotics. IEEE. Eng. Med. Biol. Mag., May/Jun. 2008;27(3):12-14.
Stoianovici, et al., MRI-Safe Robot for Endorectal Prostate Biopsy. Ieee-Asme Transactions on Mechatronics. Aug. 2014;19(4):1289-1299.
Su, et al., High-field MRI-compatible needle placement robot for prostate interventions. Stud Health Technol Inform. 2011;163:623-9.
Fischer, et al., Approaches to creating and controlling motion in MRI. Conf Proc IEEE Eng Med Biol Soc. 2011;2011:6687-90.
Stoianovici, Multi-Imager Compatible Actuation Principles in Surgical Robotics. Int J Med Robot. Jan. 2005;1(2):86-100.
Beyersdorff, et al., MR imaging-guided prostate biopsy with a closed MR unit at 1.5 T: initial results. Radiology. Feb. 2005;234(2):576-81.
Susil, et al., Transrectal prostate biopsy and fiducial marker placement in a standard 1.5T magnetic resonance maging scanner. J Urol. Jan. 2006;175(1):113-20.
Cepek, et al., A system for MRI-guided transperineal delivery of needles to the prostate for focal therapy. Med Phys. Jan. 2013;40(1):012304.
Wang, et al., MRI compatibility evaluation of a piezoelectric actuator system for a neural interventional robot. Conf Proc IEEE Eng Med Biol Soc. 2009;2009:6072-5.
Krieger, et al., Development and Evaluation of an Actuated MRI-Compatible Robotic System for MRI-Guided Prostate Intervention. IEEE ASME Trans Mechatron. Sep. 12, 2012;18(1):273-284.
Song, et al., A workspace-orientated needle-guiding robot for 3T MRI-guided transperineal prostate intervention: evaluation of in-bore workspace and MRI compatibility. Int J Med Robot. Mar. 2013;9(1):67-74.
Tokuda, et al., In-bore setup and software for 3T MRI-guided transperineal prostate biopsy. Phys Med Biol. Sep. 21, 2012;57(18):5823-40.
Sutherland, et al., Integrating an image-guided robot with intraoperative MRI: a review of the design and construction of neuroArm. IEEE Eng Med Biol Mag. May-Jun. 2008;27(3):59-65.
Zangos, et al., MR-compatible assistance system for punction in a high-field system: device and feasibility of transgluteal biopsies of the prostate gland. Eur Radiol. Apr. 2007;17(4):1118-24.
Schouten, et al., The accuracy and safety aspects of a novel robotic needle guide manipulator to perform transrectal prostate biopsies. Med Phys. Sep. 2010;37(9):4744-50.

Stoianovici, et al., A New Type of Motor: Pneumatic Step Motor. IEEE ASME Trans Mechatron. Feb. 1, 2007;12(1):98-106.
Stoianovici, et al., "MRI Stealth" robot for prostate interventions. Minim Invasive Ther Allied Technol. 2007;16(4):241-8.
Muntener, et al., Magnetic Resonance Imaging Compatible Robotic System for Fully Automated Brachytherapy Seed Placement. Urology. Dec. 2006;68(6):1313-7.
Muntener, et al., Transperineal prostate intervention: robot for fully automated MR imaging—system description and proof of principle in a canine model. Radiology. May 2008;247(2):543-9.
Althoefer, MRI-safe robots. Why are they not yet routinely used? BJU Int. Jun. 2014;113(6):975-6.
Patriciu, et al., Automatic Brachytherapy Seed Placement under MRI Guidance. IEEE Transactions on Biomedical Engineering. Aug. 2007;54(8):1499-1506.
Kanal, et al., ACR guidance document for safe MR practices: 2007. AJR Am J Roentgenol. Jun. 2007;188(6):1447-74.
Chen, et al., An MR-conditional high-torque pneumatic stepper motor for MRI-guided and robot-assisted intervention. Ann Biomed Eng. Sep. 2014;42(9):1823-33.
Tokuda, et al., Preclinical evaluation of an MRI-compatible pneumatic robot for angulated needle placement in transperineal prostate interventions. Int J Comput Assist Radiol Surg. Nov. 2012;7(6):949-57.
Van Den Bosch, et al., MRI-guided robotic system for transperineal prostate interventions: proof of principle. Phys Med Biol. Mar. 7, 2010;55(5):N133-40.
Yakar, et al., Feasibility of a pneumatically actuated MR-compatible robot for transrectal prostate biopsy guidance. Radiology. Jul. 2011;260(1):241-7.
Song, et al., Workflow Assessment of 3T MRI-guided Transperineal Targeted Prostate Biopsy using a Robotic Needle Guidance. Proceedings of SPIEE: Medical Imaging 2015: Image-Guided Procedures, Robotic Interventions, and Modeling. 2014;9036:903612.
Ukimura, et al., 3-Dimensional elastic registration system of prostate biopsy location by real-time 3-dimensional transrectal ultrasound guidance with magnetic resonance/transrectal ultrasound image fusion. J Urol. Mar. 2012;187(3):1080-6.
Kelloff, et al., Challenges in clinical prostate cancer: role of imaging. AJR Am J Roentgenol. Jun. 2009;192(6):1455-70.
Resnick, et al., Repeat prostate biopsy and the incremental risk of clinically insignificant prostate cancer. Urology. Mar. 2011;77(3):548-52.
Han, et al., Geometric Evaluation of Systematic Transrectal Ultrasound Guided Prostate Biopsy. J Urol. Dec. 2012;188(6):2404-9.
Hricak, et al., Imaging prostate cancer: a multidisciplinary perspective. Radiology. Apr. 2007;243(1):28-53.
Villers, et al., MRI in addition to or as a substitute for prostate biopsy: the clinician's point of view. Diagn Interv Imaging. Apr. 2012;93(4):262-7.
Xu, et al., Real-time MRI-TRUS fusion for guidance of targeted prostate biopsies. Comput Aided Surg. Sep. 2008;13(5):255-64.
Frye, et al., Optimizing Patient Population for MP-MRI and Fusion Biopsy for Prostate Cancer Detection. Curr Urol Rep. Jul. 2015;16(7):50.
Thoma, Prostate cancer: MRI/TRUS fusion outperforms standard and combined biopsy approaches. Nat Rev Urol. Mar. 2015;12(3):119.
Ball, et al., Safety and Feasibility of Robot-Assisted Direct MRI-Guided Transperineal Prostate Biopsy. Urology. Nov. 2017;109:216-221.
Blumenfeld, et al., Transperineal prostate biopsy under magnetic resonance image guidance: a needle placement accuracy study. J Magn Reson Imaging. Sep. 2007;26(3):688-94.
Badaan, et al., Does needle rotation improve lesion targeting? Int J Med Robot. Jun. 2011;7(2):138-47.

* cited by examiner

NEEDLE-GUIDE ROBOT WITH PRESET DEPTH OF INSERTION

CROSS REFERENCE TO RELATED APPLICATION

This application is a continuation of U.S. application Ser. No. 16/303,673 filed on Nov. 21, 2018, which claims the benefit of the 35 U.S.C. § 371 U.S. national entry of International Application PCT/US2017/033991, having an international filing date of May 23, 2017, which claims the benefit of U.S. Provisional Application No. 62/340,006, filed May 23, 2016, the content of each of the aforementioned applications is herein incorporated by reference in their entirety.

GOVERNMENT SUPPORT

The present invention was made with government support under RC 1EB010936 awarded by the National Institutes of Health. The government has certain rights in the present invention.

FIELD OF THE INVENTION

The present invention relates generally to medical devices. More particularly, the present invention relates to a needle-guide robot with a preset depth of insertion.

BACKGROUND OF THE INVENTION

Needle-guidance for diagnostic and therapy image-guided interventions can be accomplished with indirect or direct guidance methods, both having potential advantages. Direct methods use the imager at the time of the procedure. These are potentially more accurate for targeting, but special devices are needed to help the physician perform the intervention. If used in conjunction with magnetic resonance imaging (MRI) equipment, devices have very stringent compatibility requirements.

Devices for the MR have been initially classified as MRI Compatible or Incompatible, as early as 1993. While the name stuck, there was no formal definition and the classification was insufficiently descriptive. Instead, standards such as the American Society for Testing and Materials (ASTM) classify (ASTM F2503) devices for the MR environment (Table 1), and set a series of tests that these should meet (ASTM F2052, F2213, F2182, F2119). Most importantly, for clinical use in the United States compliance to these standards is mandated by the Food and Drug Administration (FDA).

TABLE 1

| ASTM F2503-13 Classification and Marking for the MR Environment | |
|---|---|
| MRI-Safe | An item that poses no known hazards resulting from exposure to any MR environment. MR Safe items are composed of materials that are electrically nonconductive, nonmetallic, and nonmagnetic. An item composed entirely of electrically nonconductive, nonmetallic and nonmagnetic materials may be determined to be MR Safe by providing a scientifically based rational rather than test data. |
| MRI-Conditional | An item with demonstrated safety in the MR environment within defined conditions. At a minimum, address the conditions of the static magnetic field, the switched gradient magnetic field and the radiofrequency fields. Additional conditions, including specific configurations of the item, may be required. Supplementary Marking—additional information that, in association with a marking as "MR Conditional" states via additional language the conditions in which an item can be used safely within the MR environment. |
| MRI-Unsafe | An item which poses unacceptable risks to the patient, medical staff or other persons within the MR environment. |

The standard points out rationally that devices made exclusively of nonconductive, nonmetallic, and nonmagnetic materials pose no known hazards in the MR environment. The standard also sets the regulatory basis for the determination of MRI safety based on this underlying scientific rationale.

Since testing a device in all MR environments is unfeasible, the standard practically excludes devices that use electricity from the MR Safe category. Several research teams have demonstrated that electrical devices (MR Conditional) can be safely used in the MRI. Since one would not have to use a device in all MR environments, proper tests in the MR equipment of choice could make the MR Conditional device a useful clinical instrument for the specific procedure. Nevertheless, devices that meet the MR Safe standard require less testing for a wider application range. Therefore, the preferential choice when developing a device for the MR is MR Safe, because this facilitates clinical translation under the regulatory protocols and a broader dissemination.

The development of devices that may operate accurately and safely in the MR environment without interfering with the functionality of the imager has been a very challenging engineering task. As such, initial devices developed for direct MRI guided procedures were manually operated. These have the merit of bringing the procedure first to clinical trials. Following research pursued the development of remotely controlled and robotic devices to facilitate the procedure. These required additional developments related to sensing and actuation, since most of the components traditionally used in robotics are MR Unsafe (e.g. electromagnetic motors). Technical developments of over a decade of research in the field have enabled building several MR Conditional and MR Safe robots. Yet few have reached the clinical trial stage.

Therefore, it would be advantageous to provide a needle-guide robot with a preset depth of insertion.

SUMMARY OF THE INVENTION

The foregoing needs are met, to a great extent, by the present invention, wherein in one aspect a method of needle insertion includes inserting a needle manually. The method includes inserting the needle through a needle-guide. The method includes limiting a direction of insertion with the needle-guide. Additionally, the method includes limiting a depth of insertion with a limiter of the needle-guide configured to preset the depth of insertion.

In accordance with an aspect of the present invention, the method includes stopping the needle assembly when it comes into contact with a stopper surface of the depth limiter at a location that corresponds to the preset depth of needle insertion. The method includes using a sterile bag to maintain sterility of the robot. The method also includes using a motor configured to set a position of the depth limiter relative to the needle-guide. Additionally, the method includes using a stepper motor.

In accordance with an aspect of the present invention, a device for needle insertion includes a needle driver device. The device includes a needle-guide. The device also includes a depth limiter.

In accordance with another aspect of the present invention, the needle-guide is a sterile and biocompatible component. A surface of the needle assembly comes into contact with a stopper surface of the depth limiter at a location that corresponds to a preset depth of needle insertion. A surface of the needle and limiter come in contact through a bag. A motor is configured to set a position of the depth limiter relative to the needle-guide. The motor is a pneumatic stepper motor. A screw mechanism is configured to set the position of the limiter. The position of the depth limiter is configured to be adjusted so that the location presets the desired depth of needle insertion. The device includes image registration markers. The device is configured to be MR-safe. A robot is include that manipulates the needle driver device. The robot is instrumented with registration markers for image-guided medical applications. The MR-Safe and MR-Unsafe components are configured to be separated. The device can include a sterile (or clean) bag, such that the entire robot is sterile.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a robot structure that includes an MRI-Safe pneumatic step motor and optical encoding technologies. The robot structure was initially built for seed brachytherapy, as a showcase of technology that can operate fully automatically with no human intervention in the MRI scanner. Preclinically this was very successful, but brachytherapy and full robotic operation were not enablers for immediate clinical translation. Therefore, the present invention was adapted for a biopsy procedure and scaled down the system to manual needle insertion. The robot structure was adapted for biopsy, a novel way of setting the depth of needle insertion, image-to-robot registration.

Figure 1:
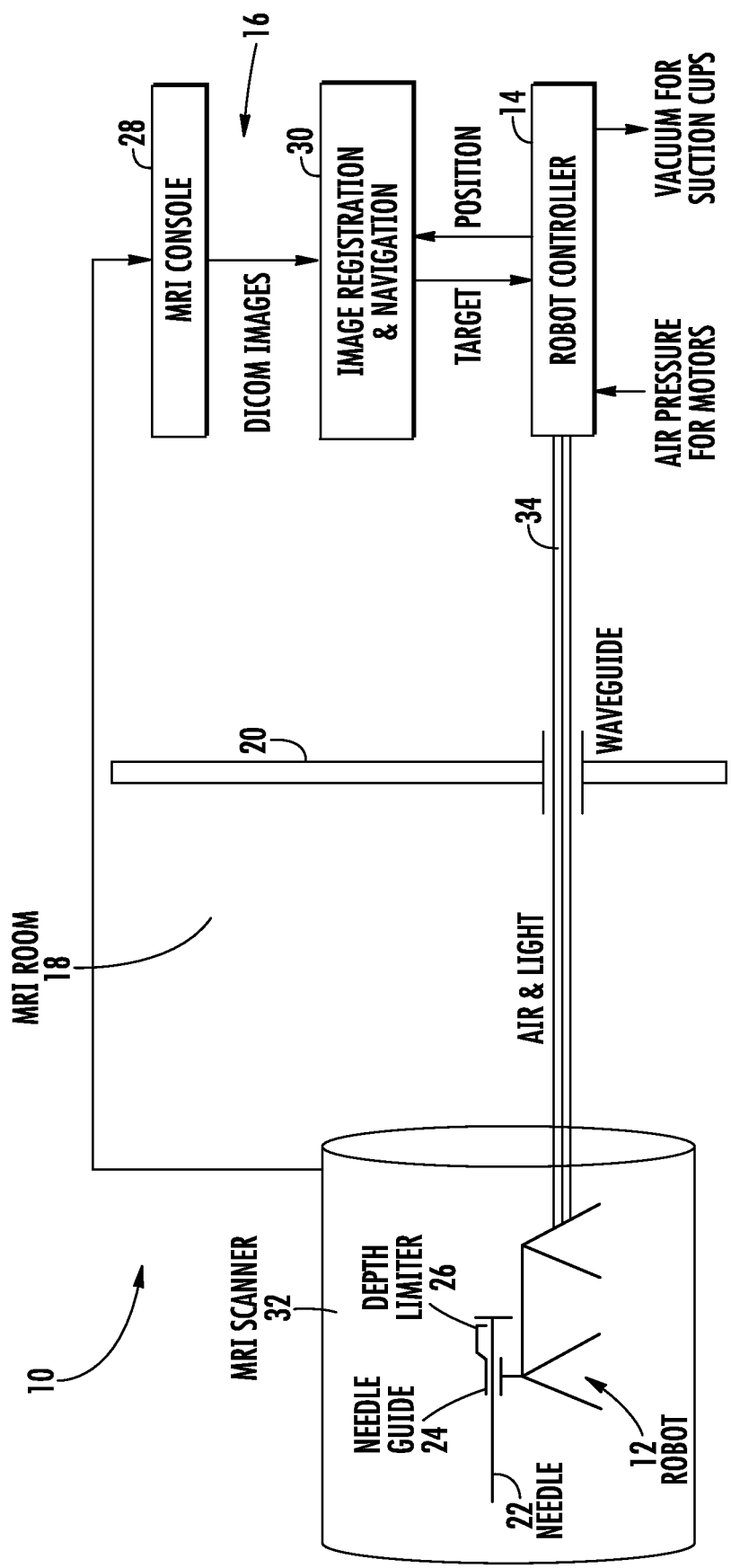
FIG. 1 illustrates a system schematic, according to an embodiment of the present invention.

The biopsy device is a 5-DoF robotically driven needle-guide and a 1-DoF depth of needle insertion limiter. The system 10 includes the robot 12, its controller 14, and a computing device16 for image registration and navigation, as shown in FIG. 1. The robot 12 goes in the MR scanner room 18 (ACR Zone IV) separated by a waveguide 20 and mounts on the MRI table. FIG. 1 illustrates a system schematic, according to an embodiment of the present invention. As illustrated in FIG. 1, the system includes the robot 12 for controlling the needle 22, needle guide 24, and depth limiter 26 within the MR scanner room 18. The MR console 28, image registration and navigation module 30, and robot controller 14 sit outside the MR scanner room 18 and allow for control of the MR scanner 32 and robot 12 within the MR scanner room 18. The robot controller can be specifically designed for the present invention, in order to provide control of the robot. The robot controller 14, MR console 28, and image registration and navigation module 30 can be incorporated into one computing device or separate computing devices and controls. If separate, the devices can be networked together either by wire or wirelessly.

Further with respect to FIG. 1, a bundle of hoses 34 including pneumatic circuits and optic fibers connect the robot 12 to its robot controller 14 located outside the MRI room 18 (ACR Zone III). The hoses 34 are passed through a standard access waveguide 20 and attach to the robot 12 with a custom-built optic and pneumatic connector. A registration marker is built within the base of the needle-guide. MM images are acquired and passed in DICOM (Digital Imaging and Communications in Medicine) format to the robot controller over the network.

If they are not incorporated into one computing device, the robot controller 14 can be located physically next to the MM console. Images showing the registration marker are used for robot-to-image registration. Target biopsy locations are selected in the MRI, and the points are mapped to robot-space coordinates based on the registration. The robot controller 14 further maps the robot-space to joint-space coordinates using the inverse kinematics of the robot 12, and controls the actuators in closed-loop position feedback. This aligns the needle-guide 24 on target for biopsy, locks the location of the needle-guide 24 in place (non-back-drivable actuators), and sets the position of the depth limiter 26. The needle 22 is then inserted manually through the needle-guide 24, up to the depth limiter 26. The biopsy is sampled manually, as usual.

Figure 2A:
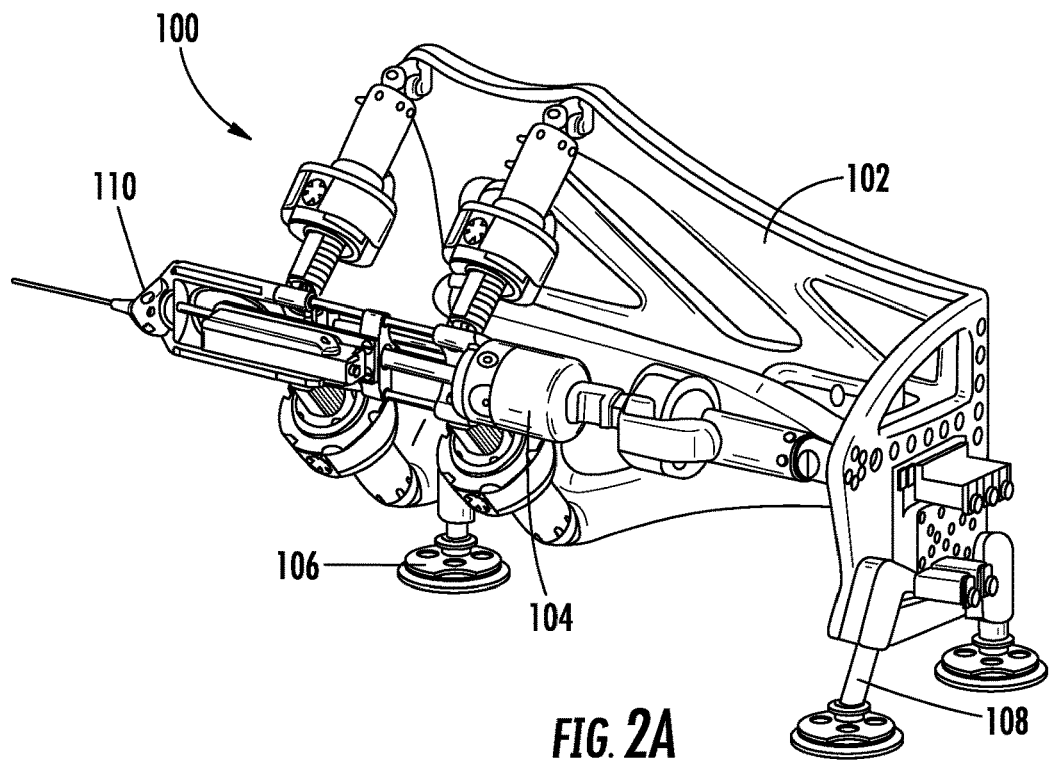
FIGS. 2A-2C illustrate views of the robot and needle driver, according to an embodiment of the present invention.
Figure 2B:
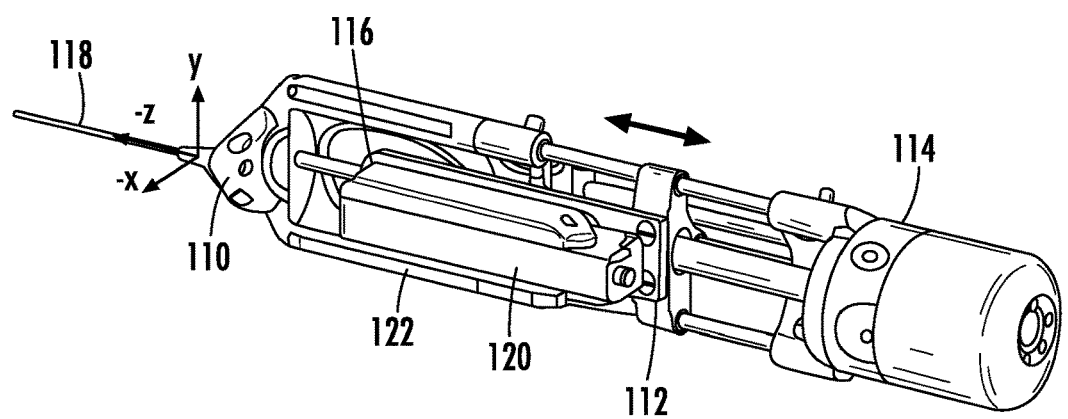
Figure 2C:
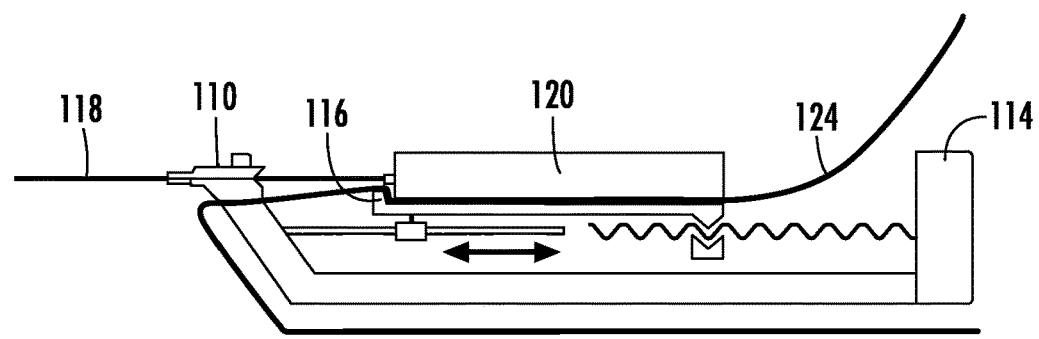

FIGS. 2A-2C illustrate views of the robot and needle driver, according to an embodiment of the present invention. The robot 100 includes the 5-DoF parallel link structure 102 of the robot 100 and a 1-DoF needle-driver 104 newly developed for biopsy, as shown in FIG. 2A. The 5-DoF parallel link structure 102 positions (3-DoF: X, Y, Z axes) and orients (2-DoF: about X, Y axes) the 1-DoF needle-driver assembly 104 with 5 linear actuators, implemented with screw drivers from rotary pneumatic stepper motors (rotary nut, sliding screw). The structure attaches with suction cups 106 to an adapter plate mounted on the MRI table. The height of the robot 100 over the table can be adjusted by the length of the suction cup mounts 108. A needle guide 110 is positioned at a distal end of the 1-DoF needle driver.

The 1-DoF needle-driver assembly and its schematic are presented in FIGS. 2B and 2C, respectively, according to an embodiment of the present invention. The needle-guide 110 is attached to the base of the driver (the platform driven by the 5-DoF parallel link), as illustrated in FIG. 2A. A slider block 112 having a stopper/limiter surface 116 is positioned by a 6th pneumatic stepper motor 114 through a screw driver (rotary screw, sliding nut). The needle 118 is passed through the needle-guide 110 until the needle handle 120 touches the stopper/limiter surface of the slider block 112, thus limiting the depth of insertion as needed to reach the target, based on the images. A registration marker 122 is included to allow for visualization of the needle 116.

The entire robot is covered with a sterile bag 124 and the only sterilized component is the needle-guide 110 (and of course the single-use needle 118). The placement of the sterile bag 124 about the driver is illustrated in FIG. 2C, which shows how the components were designed so that the needle-guide 110 attaches over the sterile bag 124 (with 2 screws) and the needle handle 120 touches the limiter through the bag. The robot is electricity-free, uses air pressure for actuation, light for the position sensors, and is entirely made of nonconductive, nonmetallic, and nonmagnetic materials. Moreover, the needle-guide, which comes in direct contact with the patient, is built of certified biocompatible material (ISO-10993).

Two types of needles can be used with the present invention, both manufactured by Invivo, Pewaukee, WI: 9896-032-02861 (11528), 18Ga×150 mm Semi-Automatic Biopsy Gun and 9896-032-05281, 18Ga×175 mm Fully Automatic Biopsy Gun (shown in FIG. 2B). Alternately, any suitable needle known to or conceivable by one of skill in the art could also be used. Accordingly, different limiters for the needle-driver were used to accommodate their different handles.

Figure 3:
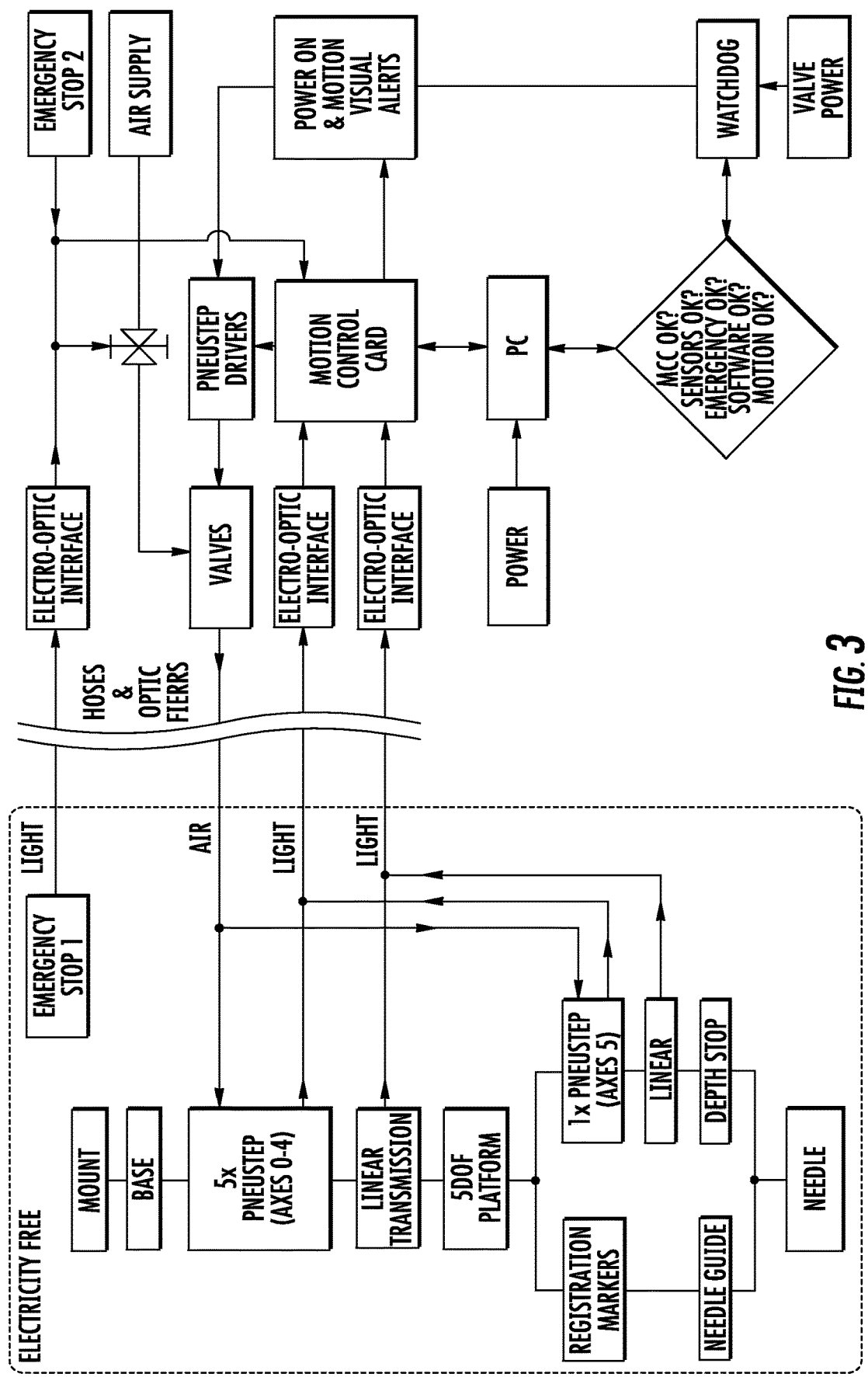
FIG. 3 illustrates a schematic diagram of a robot controller, according to an embodiment of the present invention.

FIG. 3 illustrates a schematic diagram of a robot controller, according to an embodiment of the present invention. The robot controller includes a PC running Microsoft Windows 7, a motion control card, electro-pneumatic and electro-optical interfaces, and several safety components, as illustrated in FIG. 3. The motion control card (MCC, MC-8000, PMDI, BC, Canada) presents a digital signal processor (DSP) that is responsible for axis-level coordinated motion control in real-time.

The electro-optical interface converts optical quadrature encoded signals from the pneumatic stepper motors to typical electric signals for the MCC. These are implemented with D10 Expert fiber optic sensors (Banner Engineering Corp., Minneapolis, MN, USA). Position feedback signals are used for closed-loop stepper control of each pneumatic stepper axis. Each linear actuator axis is also equipped with a limit switch, also implemented with fiber optic sensors. These are used to home the incremental encoders of the motors. The home position of the robot is shown in FIG. 2A, chosen at a central (square) position of the parallel links.

The electro-pneumatic interface includes a driver for the pneumatic stepper motor and pneumatic valves. The driver converts standard step and direction electric signals of the MCC to three electric signals that sequentially actuate three pneumatic direct acting solenoid valves (NVKF334V-5D by SMC Corp., Indianapolis, IN, USA). In turn, these generate pneumatic commutation waves that power the pneumatic stepper motor.

Safety components include a watchdog, emergency stop buttons, and visual alerts, as shown in the block diagram of the robot controller (FIG. 3). This system design has been developed according to a Risk Hazard Analysis. However, any other implementation of the system design could also be used. The watchdog has a software and a hardware component used to mitigate software errors that are possibly indeterministic. The software watchdog checks the state of several components of the system, disabling power to the pneumatic valves, should a faulty condition occur. It runs on a separate (time critical) thread and signals its continuous operation to the hardware watchdog, which suspends power after 100 ms of software watchdog inactivity.

Visual signs are used to signal the operation state of the robot. Two Emergency Stop buttons, of which one is located on the Mill table next to the patient, disable the system and suspend the pneumatic pressure through a circuit that is separate from the watchdog.

The motion control software includes axis-level motion control and robot kinematics software built in Visual C++ (Microsoft Corp, Redmond, WA). Axis-level control is implemented on the MCC is developed based on libraries of the MCC (MCI-SoftLib, PMDI). Robot kinematics has been derived based on link parameters resulting from the Computer Aided Design (CAD) of the robot.

The depth of needle insertion is also calculated based on the images and referenced in the robot CSys. The desired depth of needle insertion is calculated by referencing the depth of the needle to the center of the biopsy core slot. For the fully automated biopsy gun, the depth is also offset with the forward-fire distance of the needle. With these, the target biopsy point selected in Mill corresponds to the center of the biopsy sample. As such, in the case of the fully automated biopsy gun, the limiter sets the depth of insertion short of the target, and the target is reached only after firing the needle, as usual.

The present invention demonstrates that accurate direct MM-guided needle targeting is possible. In the human trials, the robot was capable of 2.97 mm 3D accuracy and 2.55 mm in a plane normal to the needle. For PCa the required accuracy is probably <5 mm, since a clinical significant tumor (0.5 cm$^3$) has a 5 mm radius if spherical. Targeting errors include numerous components which are often cumulative: image geometry errors, registration errors, robot position errors, robot structural deformations under load, and never the less needle deflections. A detailed error component analysis is therefore helpful, and all components that can be minimized/mitigated should. For example, to finally keep the needle within 5 mm of the target: pneumatic stepper motor (37W) linear step 0.055 mm, a stiff parallel-link structure, bench tests of motion 0.076±0.035 mm, linear motion in a 7T MRI scanner 0.047±0.053 mm, motion repeatability 0.060 mm, placing seeds in agar models 0.72±0.36 mm and under 3T MRI guidance 1.2 mm (SD 0.4 mm), targeting under 3T Mill in an animal model with needle accuracy of 2.02 mm (range 0.86-3.18 mm) and seed placement accuracy of 2.50 mm (range 1.45-10.54 mm), and registration errors of 0.25 mm (SD 0.31 mm) reported herein.

The robot of the present invention presents a 5-DoF parallel link structure to position and orient a needle-guide and a 1-DoF stopper to limit the depth of manual needle insertion. The limiter feature and its arrangement under the sterile bag is novel and reduces the number of sterile components to the needle-guide alone. In most image-guided robots and all 4 that were used clinically the depth is decided by the operator who typically looks up the marks on the needle. This is adequate since accurate control of the needle depth for biopsy is not critical. The length of the biopsy slot (typically 17 mm) is forgiving for errors in depth (perhaps within (17-10)/2=+3.5 mm). For this most needle targeting studies report the normal plane values alone. With the actuated limiter, the depth is also very accurately controlled, as shown by the small difference between the accuracies in 3D (2.97 mm) and normal plane (2.55 mm). The automation reduces the workload of the operator who manipulates the biopsy needle in a tight space of the MRI scanner gantry and the possibility of errors. Also, the improved accuracy could be helpful for other procedures such as ablations where depth may be critical. The achieved MRI-based targeting accuracy of 2.55 mm of the present invention is outstanding.

The movement and actuation of the present invention can be carried out using a computer, non-transitory computer readable medium, or alternately a computing device or non-transitory computer readable medium incorporated into the robotic device or the imaging device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer for the imaging device or the robotic device. The operating console for the imaging device or the robotic device is a non-generic computer specifically designed by the manufacturer. It is not a standard business or personal computer that can be purchased at a local store. Additionally, the console computer can carry out communications with the scanner through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of needle insertion with a robot comprising:
   inserting a needle manually;
   inserting the needle through a needle-guide;
   limiting a direction of insertion with the needle-guide, wherein the direction of insertion can be preset using the needle guide;
   limiting a depth of insertion with a depth limiter of the needle-guide, wherein the depth of insertion can be preset using the limiter, wherein a body of the needle contacts the depth limiter, and the depth limiter thereby limits the depth of the insertion of the needle, and wherein a needle driver device actuates the needle-guide and the depth limiter.

2. The method of claim 1 further comprising stopping the needle when it comes into contact with a stopper surface of the depth limiter at a location that corresponds to the preset depth of needle insertion.

3. The method of claim 1 further comprising using a sterile bag to maintain sterility of the robot.

4. The method of claim 1 further comprising using a motor configured to set a position of the depth limiter relative to the needle-guide.

5. The method of claim 4 further comprising using a stepper motor.

6. A method of needle insertion with a robot comprising:
   limiting a direction of insertion of a needle through a needle guide, wherein the direction of insertion can be preset using the needle guide;
   limiting a depth of insertion with a depth limiter of the needle-guide, wherein the depth of insertion can be preset using the limiter, wherein a body of the needle contacts the depth limiter, and the depth limiter thereby limits the depth of the insertion of the needle, and wherein a needle driver device actuates the needle-guide and the depth limiter.

* * * * *